(12) United States Patent
Bragg et al.

(10) Patent No.: US 6,762,841 B1
(45) Date of Patent: Jul. 13, 2004

(54) METHOD OF PERFORMING SPECTRAL ANALYSIS IN A PHARMACEUTICAL DISSOLUTION PROCESS

(75) Inventors: Susan L. Bragg, University City, MO (US); Danny D. Meyer, St. Louis, MO (US)

(73) Assignee: SpectraAlliance, Inc., St. Louis, MO (US)

( * ) Notice: Subject to any disclaimer, the term of this patent is extended or adjusted under 35 U.S.C. 154(b) by 0 days.

(21) Appl. No.: 09/507,850

(22) Filed: Feb. 22, 2000

(51) Int. Cl.[7] .......................... G01N 21/00; G01N 1/10
(52) U.S. Cl. ........................................ 356/436; 356/246
(58) Field of Search ..................... 356/246, 436–440, 356/441

(56) References Cited

U.S. PATENT DOCUMENTS 5,039,224 A * 8/1991 O'Rourke et al. .......... 356/434
5,404,218 A * 4/1995 Nave et al. ................. 356/246
5,485,270 A * 1/1996 Freud et al. ................ 356/336
5,510,895 A * 4/1996 Sahagen .................... 356/436

* cited by examiner

*Primary Examiner*—Frank G. Font
*Assistant Examiner*—Amanda Merlino
(74) *Attorney, Agent, or Firm*—Thompson Coburn LLP

(57) ABSTRACT

A method for performing spectral analysis in a pharmaceutical dissolution process. The method comprises inserting a fiber optic probe of a spectral analyzer into a dissolution vessel. The dissolution vessel contains a dissolution medium. The probe has a launch cable, a return cable, a launch lens portion, a return lens portion and a reflector. The reflector is spaced from both the lens portions. The cables, lens portions and reflector are arranged and adapted to form a light pathway whereby light transmitted through the launch cable passes through the launch lens portion, through a volume of the dissolution medium in the spacing between the launch lens portions and the reflector, and then through the return cable. The spacing between the reflector and the lens portions comprise a sample region. The fiber optic probe is sized and adapted to prevent bubbles in the dissolution medium from being trapped in the sample region. The method further comprises transmitting light along the optic pathway, and analyzing the transmitted light for determining certain optical properties of the dissolution medium in the optic pathway.

20 Claims, 2 Drawing Sheets

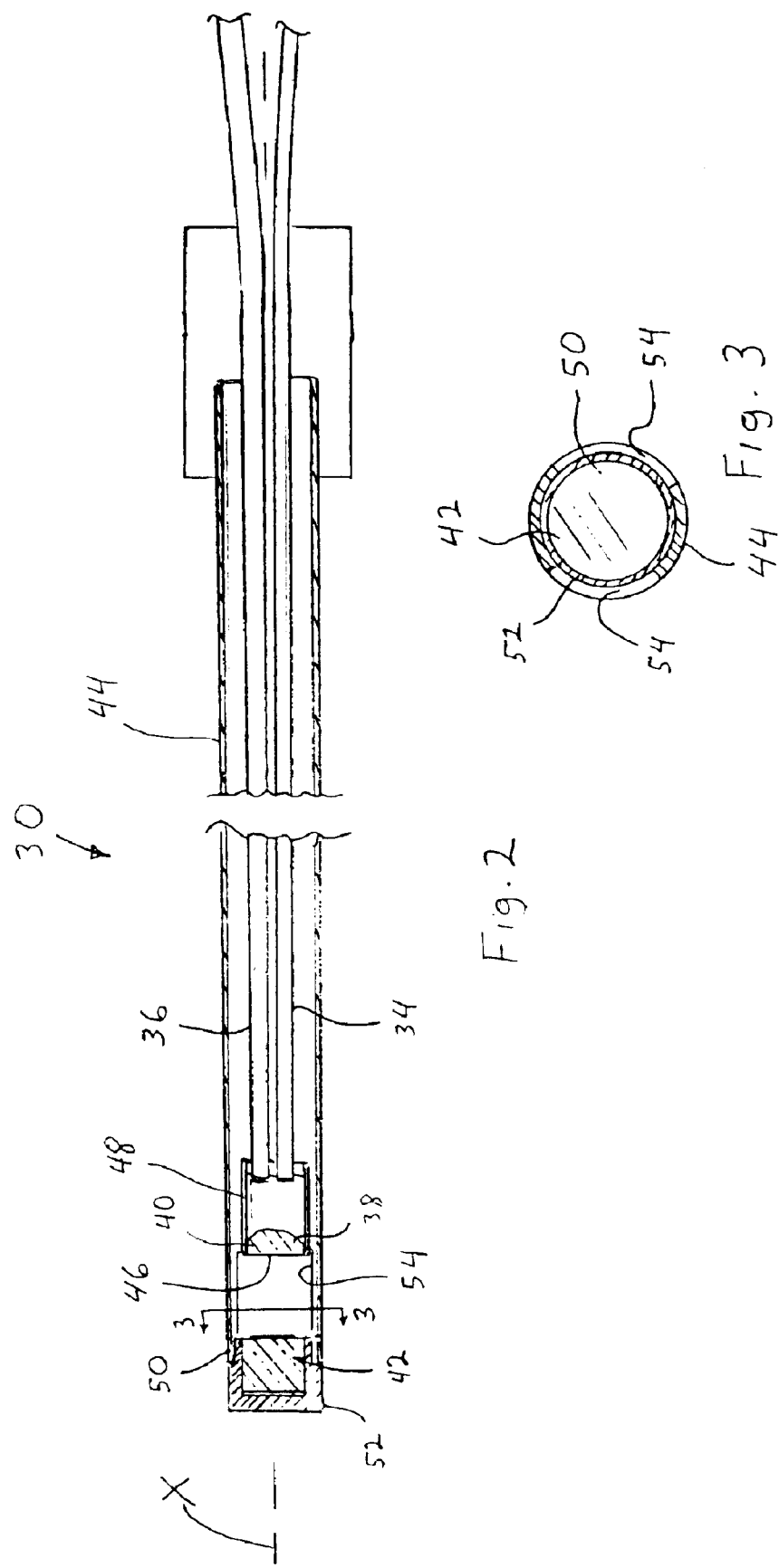

METHOD OF PERFORMING SPECTRAL ANALYSIS IN A PHARMACEUTICAL DISSOLUTION PROCESS

BACKGROUND OF THE INVENTION

This invention relates generally to methods of performing spectral analysis in a pharmaceutical dissolution process, and more particularly to such methods using fiber optic probes.

Dissolution monitoring is used to determine the concentration of a pharmaceutical active ingredient as a function of time. Dissolution testing is an FDA requirement and an important step in the drug development process. A tablet, for example, is dropped into a temperature-controlled reservoir containing an aqueous solution. The concentration of the active ingredient in solution is measured as the tablet dissolves. The concentration can be determined through an optical spectroscopic measurement, primarily in the ultraviolet to visible portion of the spectrum. The sample is either removed from the reservoir for measurement or an in situ measurement probe is inserted into the reservoir.

In situ measurements offer increased measurement efficiency, while potentially reducing measurement errors due to extraction. In situ probes use fiber optic coupling to connect the measurement probe to both the light source and the detecting spectrometer.

Dissolution testing is usually performed automatically using apparatus designed to sample continuously or discretely from dissolution vessels. In a continuous sampling procedure, a single fiber optic probe per dissolution vessel is employed. In a discrete sampling procedure, a fiber optic probe is used for sampling in a plurality of dissolution vessels. A robot arm dips the probe in a first dissolution vessel where optic measurements are made to measure certain properties of a dissolution solution in the dissolution vessel. The robot arm then moves the probe from the first dissolution solution to a bath where the probe is cleaned, and then dips the probe into a second dissolution vessel for measuring certain properties of a second dissolution solution.

A disadvantage of prior art probes used in dissolution testing is that air occasionally becomes trapped in a sampling region of the probe (e.g., adjacent a lens or window). The trapped air impedes accurate spectral analysis of the dissolution solution.

SUMMARY OF THE INVENTION

Among the objects and advantages of the present invention may be noted the provision of an improved method for performing spectral analysis in a pharmaceutical dissolution process; and the provision of such a method employing a fiber optic probe which minimizes entrapment of air within the probe sample region.

Generally, a method of the present invention is for performing spectral analysis in a pharmaceutical dissolution process. The method comprises inserting a fiber optic probe of a spectral analyzer into a dissolution vessel. The dissolution vessel contains a dissolution medium. The probe has a launch cable, a return cable, a launch lens portion, a return lens portion and a reflector. The cables, lens portions and reflector are arranged and adapted to form a light pathway whereby light transmitted through the launch cable passes through the launch lens portion, through a volume of the dissolution media in the spacing between the launch lens portions and the reflector, then through the return cable. The spacing between the reflector and the lens portions comprise a sample region. The fiber optic probe is sized and adapted to prevent bubbles in the dissolution media from being trapped in the sample region. The method further comprises transmitting light along the optic pathway, and analyzing the transmitted light for determining certain optical properties of the dissolution media in the sample region.

Another aspect of the present invention is a method of making a fiber optic probe. The method comprises placing into a sheath a launch cable, a return cable, a launch lens portion, a return lens portion, and a reflector. The launch lens portion is forward of and aligned with the launch cable. The return lens portion is forward of and aligned with the return cable. The launch lens portion has a focal length substantially equal to the focal length of the return lens portion. The sheath has an end margin extending forward from the lens portions and terminating in a sheath end. The end margin of the sheath has at least one slot therein. The method further comprises: positioning a reflector element adjacent the sheath end and spaced from the lens portions by the desired sample region length; placing the return cable into optical communication with an optical detector; transmitting light along the launch cable through the launch lens portion and to the reflector element; adjusting the position of the reflector element relative to the sheath to substantially maximize detection by the detector of the transmitted light reflected from the reflector through the return lens portion and through the return cable and to the detector; and securing the reflector element to the sheath to maintain the reflector element in its adjusted position.

Other objects and features will be in part apparent and in part pointed out herinafter.

BRIEF DESCRIPTION OF THE DRAWINGS

FIG. 2 is an enlarged, longitudinal, cross-sectional view of a fiber optic probe of the spectral analyzer of FIG. 1; and FIG. 3 is a cross-sectional view taken along the plane of line 3—3 of FIG. 2.

Corresponding reference characters indicate corresponding parts throughout the several views of the drawings.

DESCRIPTION OF THE PREFERRED EMBODIMENT

Figure 1:
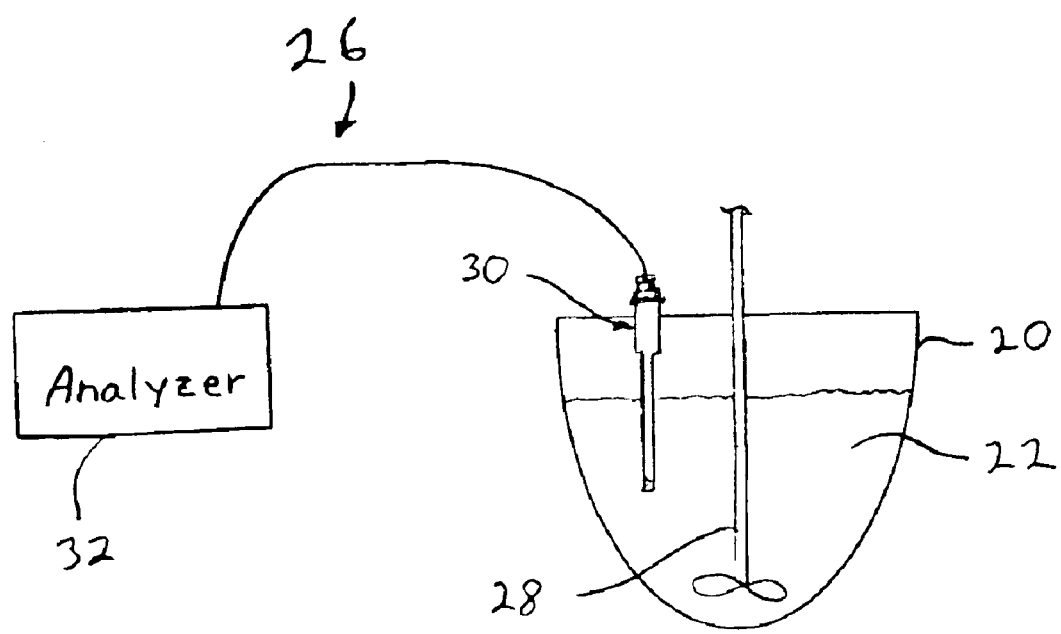
FIG. 1 is a schematic of a dissolution system of the present invention, the dissolution system comprising a dissolution vessel containing a dissolution media, and a spectral analyzer.

Referring to FIG. 1, a dissolution process of the present invention employs a dissolution vessel 20, a dissolution medium 22 contained within the dissolution vessel, a paddle 28 extending into the vessel for mixing the dissolution medium 22, and a spectral analyzer, generally indicated at 26. The dissolution medium 22 is preferably simulated biological fluids with pharmaceutical formulations being dissolved therein. A paddle 28 extends into the dissolution medium 22 for mixing the dissolution medium. The spectral analyzer 26 includes a fiber optic probe, generally indicated at 30, and an analyzer 32. The probe 30 is adapted to extend downward into the dissolution media and is in optic communication with the analyzer 32. Light energy from the analyzer 32 is transmitted along an optical pathway via the probe 30 through a sample of the dissolution medium 22 and returned to the analyzer where it is analyzed for determining certain optical properties of the dissolution medium. The optical properties may enable a user to determine release rates and/or other properties of the pharmaceutical formulations.

Referring now to FIG. 2, the probe 30 comprises a launch (or lamp) cable 34, a return (or detector) cable 36, a launch lens portion 38 aligned with the launch cable, a return lens portion 40 aligned with the return cable, a reflector element 42, and a sheath 44. The cables 34, 36, the lens portions 38, 40 and the reflector 42 are arranged and adapted to form a light pathway whereby light transmitted through the launch cable passes through the launch lens portion, through a volume of the dissolution media in the spacing between the launch lens portions and the reflector, through the return lens portion, through the return cable and to a detector (not shown) of the analyzer 32.

Each of the launch and return cables 34, 36 are preferably conventional fiber optic cables having one or more fibers. The fiber optic cables may also be specialized cables, such as those that minimize solarization. The cables 34, 36 extend into the sheath 44 generally along a probe axis X. The cables 34, 36 are of sufficient length to allow easy attachment to the spectral analyzer and are terminated with a conventional fiber optic connector, such as an SMA 905. The cables 34, 36 are supported and strain relieved at the rearward end of the probe by a handle assembly 56. The launch and return lens portions 38, 40 are preferably portions of a single monolithic lens 46. Alternatively, the launch and return lens portions 38, 40 may be separate lenses. Preferably, the lens 46 is of a synthetic fused silica. Alternatively, the lens 46 could be of sapphire, quartz or any other suitable lens material. The lens 46 is preferably secured to a forward end of a lens/fiber holder assembly 48, and forward ends of the cables 34, 36 are preferably secured to a rearward end of the holder assembly. Cables 34, 36 are preferably spaced from the lends 46 by a distance equal to the focal length of the lens 46. The reflector element 42 preferably includes a mirror 50 secured to a mirror holder 52. The mirror 50 preferably includes a highly reflective surface. The reflector element 42 is secured to a forward end of the sheath 44 and is preferably spaced from the lens by the desired sample region path length. Although the reflector element 42 preferably includes a mirror, it is to be understood that other components could be used instead of the mirror without departing from the scope of this invention. For example, the reflector element could instead comprise a prism (not shown) configured to reflect light from the launch lens portion to the return lens portion. The sheath 44 includes at least one and preferably two slots (or openings) 54 (only one of which is shown in FIG. 2) for permitting fluid (e.g., the dissolution medium) to flow between the lens 46 and mirror 50. The slots 54 are preferably on opposite sides of a forward end margin of the sheath 44 to allow fluid to flow through the end margin of the sheath. Also preferably, the slots 54 extend from the lens 46 forward to the mirror 50.

The fiber optic probe 30 is sized and adapted to prevent bubbles in the dissolution medium from being trapped in the sample region (e.g., from being trapped against the surface of the lens 46). Preferably, each cross-sectional dimension of the probe 30 lying in a plane perpendicular to the probe axis X and between the reflector element 42 and the lens 46 are equal to or less than approximately 5 millimeters (mm), and more preferably equal to or less than approximately 4 mm. In the preferred embodiment, such a cross-sectional sectional view is shown in FIG. 3. In this embodiment, the largest such cross-sectional dimension is the outer diameter of the sheath 44. Thus, the outer diameter of the shroud is preferably equal to or less than approximately 5 mm, and more preferably equal to or less than approximately 4 mm. The small diameter of the probe 30 confers many features. The probe 30 is minimally invasive; its small diameter makes accurate measurements possible without perturbing the system to be measured. In addition, the small diameter of the probe means that the sample volume (i.e., the volume between the lens 46 and mirror 50 and bounded by the sheath 44) is much smaller than conventional probes used in dissolution testing. The sample volume is only 40% as large as that of a probe having a ¼" (6.3 mm) diameter, and only 10% as large as that of a probe having a ½" (12.7 mm) diameter. This small volume (about 12 $mm^3$ for a 10 mm optical path-length probe means that a concomitantly smaller volume of air has the opportunity to be trapped within the sample volume when the probe is inserted. A smaller volume of trapped air reduces the likelihood of producing bubbles on the probe optics.

Air bubbles formed in liquids also tend to have characteristic dimensions that depend on the properties of the liquid. Bubbles tend to form in the lowest energy configuration possible, with a larger bubble having a lower energy. Small bubbles may coalesce to form larger bubbles. The small diameter of the probe 30 does not physically support large bubbles, if they should form during probe insertion. Large bubbles will tend to float off, or break, rather than be trapped by the probe optics. Larger diameter probes better support and retain large diameter bubbles which have been formed during insertion.

In making the fiber optic probe 30, the launch cable 34, return cable 36, lens 46, and the reflector element 42 are placed into the sheath 44. The launch lens portion 38 of the lens 46 is forward of and spaced from the launch cable 34. The return lens portion 40 of the lens 46 is forward of and spaced from the return cable 36. The launch lens portion 38 preferably has a focal length substantially equal to the focal length of the return lens portion 40. The lens 46 is preferably secured via the lens holder 48 to the sheath and in with the slots 54. Cables 34, 36 are preferably secured in lens holder 48 rearward of the lens portions at a distance approximately equal to the focal length of the lends 46. The reflector element 42 is positioned adjacent the sheath end (i.e., the forward-most end, or the left-most end as viewed in FIG. 2) of the sheath and spaced from the lens 46 a distance corresponding the desired sample path length, for example 5 mm. The return cable 36 is placed into optical communication with the optical detector of the analyzer 32. Light energy is then preferably transmitted along the launch cable 34 through the lens 46 and to the reflector element 42. The position of the reflector element 42 relative to the sheath 44 is then adjusted to substantially maximize detection by the detector of the transmitted light reflected from the reflector through the return lens portion and through the return cable and to the detector. In other words, the reflector element 42 is tilted and/or moved axially along the probe axis X until the maximum amount of reflected light energy is transmitted through the return cable 36 to the detector. The reflector element 42 is then permanently secured in such position to the sheath to maintain the reflector element in such position. Preferably, the reflector element 42 is secured to the sheath via a suitable, chemical-resistant epoxy such as that sold by product number EP21ARSP-1, commercially available from Masterbond, of Hackensack, N.J.

In operation, the launch cable 34 of the probe 30 is in optical communication with a light source (not shown) in the analyzer 32, and the return cable 36 is in optical communication with a detector (not shown) of the analyzer. The forward-most portion of the probe 30 is inserted into the dissolution medium 22 in the dissolution vessel 20. Light energy is transmitted from the light source, through the launch cable 34, through the lens 46, through the dissolution media between the lens and reflector element 42 and to the reflector element where it is reflected through the dissolution medium again, then to the lens and transmitted to the detector via the return cable 36. The transmitted light received by the detector is then analyzed for determining the optical properties of the dissolution media.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. A method of performing spectral analysis in a pharmaceutical dissolution process, the method comprising:

inserting a fiber optic probe of a spectral analyzer into a dissolution vessel, the dissolution vessel containing a dissolution medium, the probe having a launch cable, a return cable, a launch lens portion, a return lens portion and a reflector, the reflector being spaced from both the lens portions, the cables, lens portions and reflector being arranged and adapted to form a light pathway whereby light transmitted through the launch cable passes through the launch lens portion, through a volume of the dissolution media in the spacing between the launch lens portions and the reflector, through the return lens portion, and then through the return cable, the spacing between the reflector and the lens portions comprising a sample region, the fiber optic probe being sized and adapted to prevent bubbles in the dissolution media from being trapped in the sample region;

transmitting light along the optic pathway;

analyzing the transmitted light for determining certain optical properties of the dissolution media in the sample region.

2. A method as set forth in claim 1 wherein the probe further comprises a sheath portion, the sheath portion containing the lens portions and reflector, the sheath portion having a diameter equal to or less than approximately 5 mm.

3. A method as set forth in claim 2 wherein the sheath portion has a diameter equal to or less than approximately 4 mm.

4. A method as set forth in claim 1 wherein the launch lens portion and the return lens portion are portions of a single monolithic lens.

5. A method as set forth in claim 1 wherein the launch and return cables extend generally along a probe axis, each cross-sectional dimension of the probe lying in a plane perpendicular to the probe axis and between the reflector and the lens portions is equal to or less than approximately 5 mm.

6. A method as set forth in claim 1 wherein the launch and return cables extend generally along a probe axis, each cross-sectional dimension of the probe lying in a plane perpendicular to the probe axis and between the reflector and the lens portions is equal to or less than approximately 4 mm.

7. A method as set forth in claim 1 wherein the reflector is a mirror.

8. A method as set forth in claim 1 wherein the launch lens portion is generally aligned with an end of the launch cable, and wherein the return lens portion is generally aligned with an end of the return cable.

9. A method of performing spectral analysis in a pharmaceutical dissolution process, the method comprising:

inserting a fiber optic probe of a spectral analyzer into a dissolution vessel, the dissolution vessel containing a dissolution medium, the probe having a launch cable, a return cable, a launch lens portion, a return lens portion and a reflector, the launch and return cables extending generally along a probe axis, the reflector being spaced from both the launch lens portion and the return lens, the cables, lens portions and reflector being arranged and adapted to form a light pathway whereby light transmitted through the launch cable passes through the launch lens, through a volume of the dissolution medium in the spacing between the lens portions and the reflector, through the return lens, and then through the return cable, the spacing between the reflector and the lens portions comprising a sample region, each cross-sectional dimension of the probe lying in a plane perpendicular to the probe axis and between the reflector and the lens portions being equal to or less than approximately 5 mm;

transmitting light along the optic pathway;

analyzing the transmitted light for determining certain optical properties of the dissolution media in the sample region.

10. A method as set forth in claim 9 wherein the launch lens portion is generally aligned with a forward end of the launch cable, and wherein the return lens portion is generally aligned with a forward end of the return cable.

11. A method as set forth in claim 10 wherein each cross-sectional dimension of the probe lying in a plane perpendicular to the probe axis and between the reflector and the lens portions is equal to or less than approximately 4 mm.

12. A method as set forth in claim 10 wherein the probe further comprises a sheath portion, the sheath portion containing the lens portions and reflector, the sheath portion having a diameter equal to or less than approximately 5 mm.

13. A method as set forth in claim 12 wherein the sheath portion has a diameter equal to or less than approximately 4 mm.

14. A method of making a fiber optic probe comprising:

placing into a sheath a launch cable, a return cable, a launch lens portion, a return lens portion, and a reflector, the launch lens portion being forward of and aligned with the launch cable, the return lens portion being forward of and aligned with the return cable, the launch lens portion having a focal length substantially equal to the focal length of the return lens portion, the sheath having an end margin extending forward from the lens portions and terminating in a sheath end, the end margin of the sheath having at least one slot therein;

positioning a reflector element adjacent the sheath end;

placing the return cable into optical communication with an optical detector;

transmitting light along the launch cable through the launch lens portion and to the reflector element;

adjusting the position of the reflector element relative to the sheath to substantially maximize detection by the detector of the transmitted light reflected from the reflector through the return lens portion and through the return cable and to the detector;

securing the reflector element to the sheath to maintain the reflector element in its adjusted position.

15. A method as set forth in claim 14 wherein the slot extends forward to the reflector element.

16. A method as set forth in claim 14 wherein the sheath has a diameter equal to or less than approximately 5 mm.

17. A method as set forth in claim 14 wherein the sheath has a diameter equal to or less than approximately 4 mm.

18. A method as set forth in claim 14 wherein the launch lens portion and the return lens portion are portions of a single monolithic lens.

19. A method as set forth in claim 1 wherein the launch lens portion is spaced from the launch cable and the return lens portion is spaced from the return cable.

20. A method as set forth in claim 9 wherein the launch lens portion is spaced from the launch cable and the return lens portion is spaced from the return cable.

* * * * *